(12) United States Patent
Hyodo et al.

(10) Patent No.: US 7,509,872 B2
(45) Date of Patent: Mar. 31, 2009

(54) STRESS AND STRAIN ANALYSIS METHOD AND ITS EQUIPMENT

(75) Inventors: Koji Hyodo, Ibaraki (JP); Chao-Nan Xu, Saga (JP); Takashi Yamane, Ibaraki (JP); Motoyuki Akamatsu, Ibaraki (JP); Yoshiyuki Yokogawa, Aichi (JP); Tetsuya Kameyama, Aichi (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 149 days.

(21) Appl. No.: 11/655,219

(22) Filed: Jan. 19, 2007

(65) Prior Publication Data

US 2007/0186674 A1    Aug. 16, 2007

(30) Foreign Application Priority Data

Jan. 20, 2006    (JP)    ............................. 2006-011844

(51) Int. Cl.
*G01N 3/08*    (2006.01)
(52) U.S. Cl. .............................. 73/800; 73/826; 356/34
(58) Field of Classification Search .................. 73/800, 73/762, 826; 257/77; 356/32, 34; 250/458.1
See application file for complete search history.

(56) References Cited

U.S. PATENT DOCUMENTS

| | | | | |
|---|---|---|---|---|
| 4,786,802 A * | 11/1988 | Yoshii et al. | ............... | 250/225 |
| 4,914,487 A * | 4/1990 | Croizer et al. | ............... | 356/35 |
| 5,519,486 A * | 5/1996 | Baird et al. | ............... | 356/35.5 |
| 6,055,053 A * | 4/2000 | Lesniak | ...................... | 356/366 |
| 6,159,394 A * | 12/2000 | Akiyama et al. | ...... | 252/301.4 R |
| 6,499,355 B1 * | 12/2002 | Potyrailo | ..................... | 73/762 |
| 6,628,375 B2 * | 9/2003 | Xu et al. | ....................... | 356/32 |
| 6,763,727 B2 * | 7/2004 | Miragliotta et al. | ........... | 73/800 |
| 7,060,371 B2 | 6/2006 | Akiyama et al. | | |
| 2001/0017059 A1 * | 8/2001 | Xu et al. | ....................... | 73/800 |
| 2005/0247912 A1 * | 11/2005 | Akiyama et al. | ...... | 252/301.4 R |
| 2005/0266269 A1 * | 12/2005 | Imai et al. | ................... | 428/698 |
| 2006/0035079 A1 * | 2/2006 | Xu et al. | ..................... | 428/402 |
| 2008/0120045 A1 * | 5/2008 | Hyodo et al. | ................. | 702/42 |

FOREIGN PATENT DOCUMENTS

| | | |
|---|---|---|
| JP | 11-120801 A | 4/1999 |
| JP | 2001-215157 A | 8/2001 |
| JP | 2003-137622 A | 5/2003 |

* cited by examiner

*Primary Examiner*—Harshad Patel
*Assistant Examiner*—Freddie Kirkland, III
(74) *Attorney, Agent, or Firm*—Sughrue Mion, PLLC

(57) ABSTRACT

Provided are a stress analysis method and stress analysis equipment that enable a detailed stress measurement, by using both a photoelasticity measurement method and a stress measurement (mechanoluminescence measurement) which utilizes a mechanoluminescent substance to measure a stress state of an object. Physical quantities that are measurable include individual principal stress component and a principal stress direction. The photoelasticity measurement method alone cannot measure individual principal stress component values.

8 Claims, 2 Drawing Sheets

STRESS AND STRAIN ANALYSIS METHOD AND ITS EQUIPMENT

BACKGROUND OF THE INVENTION

1. Field of the Invention

The present invention relates to a stress and strain analysis method and stress and strain analysis equipment that enable a more detailed determination of a stress and strain state of an object.

2. Description of the Related Art

Safety from a dynamic viewpoint in various products such as airplanes, trucks, piping in power plants, bridges, and orthopedic and dental implants is a basic and indispensable element for realizing a worry-free and safe society. Also, for realization and evaluation of safety of the products from the dynamic viewpoint, a stress and strain measurement technology plays an important role.

Conventionally, a strain gauge method has been used for measurement of a stress distribution. In the strain gauge method, many strain gauges are stuck to a surface of a measurement target object, and a stress and strain distribution is determined based on an output signal from each strain gauge at the time of application of a load. With this method, quantitative measurement is possible but in the case of a wide measurement area or a narrow measurement area, a thorough measurement is impossible due to a limit on the number of gauges that can be stuck in the area.

Therefore, a photoelasticity measurement method has also been used. In the photoelasticity measurement method, a stress distribution is measured by utilizing a temporary photobirefringent property that occurs in accordance with the amount of a stress at the time of application of a load to a sample. There are various photoelasticity measurement methods such as a method in which measurement is conducted using a transparent model with a similar shape to a real sample, and a method in which measurement is conducted by forming a photoelastic coating for a surface of a real sample. Each of those methods has a feature that it is possible to measure a stress as an image.

Meanwhile, an applicant of the present invention has studied an inorganic material that emits light in response to mechanical energy and have succeeded in manufacturing a material, including a base material that is a piezoelectric body having, in particular, a wurtzite structure and an inorganic substance having a luminescence center, as described in Japan Patent Publication No. 11-120801 A (Japan Patent No. 3-265356 B). The applicant of the present invention has found that it is possible to dramatically improve the light intensity emitted from an obtained thin film by adding an inorganic substance to the base material described above and have filed a patent application. Thereafter, as a result of a further study, the applicant of the present invention has found various inorganic substances that emit light in response to such forces (mechanoluminescence material), as disclosed in U.S. Pat. No. 7,060,371, and are also conducting a study for using such substances in various fields. For instance, as disclosed in JP 2003-137622 A, the applicant of the present invention propose a technique of detecting an abnormal stress that is a harbinger of destruction of concrete by mixing a mechanoluminescence material into the concrete.

As described above [04], in the photoelasticity measurement method, a stress distribution of an object is measured as an image. For instance, in the photoelasticity measurement method by a general plane polariscope, the light intensity I observed after passing an analyzer is expressed as follows:

$$I = I_0 \sin^2 2\Psi \sin^2(\rho/2) \tag{1}$$

where $I_0$: incident light intensity,
$\Psi$: principal stress direction of a sample, and
$\rho$: relative phase difference.

Here, the relative phase difference $\rho$ and a fringe order N are expressed as follows:

$$\rho = 2\pi\alpha t(\sigma_1 - \sigma_2), \text{ and} \tag{2}$$

$$N = \alpha t(\sigma_1 - \sigma_2) \tag{3}$$

where
$\alpha$: photoelasticity sensitivity, and
t: thickness of the sample.

The photoelasticity sensitivity $\alpha$ is expressed by the following equation:

$$\alpha = 2\pi C/\lambda \tag{4}$$

where
C: Brewster's constant, and
$\lambda$: light wavelength.

As expressed by Equations (1) to (4), with this technique, two information items are obtained. That is, at the time when $\Psi$ is equal to 0 or $\pi/2$, a principal stress direction can be found from a black fringe (isoclinic line), in which a principal stress axis coincides with an optical axis at a point where I is equal to 0, and a principal stress difference can be found from a black fringe (isochromatic line) that becomes a positive integer (such as N=0, 1, 2 . . . ).

This technique, however, has a fundamental limitation in that it is impossible to obtain individual stress component values $\sigma_1$ and $\sigma_2$.

SUMMARY OF THE INVENTION

Therefore, an object of the present invention is to provide a stress analysis method and stress analysis equipment, which allow a more detailed stress measurement than can be provided by a photoelasticity measurement method alone by using both the photoelasticity measurement method and a stress measurement, which utilizes a mechanoluminescence material, to measure a state of a stress of an object.

In order to solve the above-mentioned problem [09], the applicants of the present invention have found a technique of applying a substance that emits light in response to mechanical energy, which has been developed by the applicant of the prsent invention in the past as described above [05], for stress measurement. More specifically, the present invention provides a technique that uses a photoelasticity stress measurement method and a method (defined as the "mechanoluminescence measurement method") in which a mechanoluminescence substance is applied to an object through application, mixing, or the like, light emitted in response to a load is captured with light detecting equipment (such as a camera), and a stress distribution or the like is measured. That is, the stress analysis method according to the present invention includes: measuring a state of a stress which acts on a measurement target object by measuring photobirefringence of a substance caused by the stress (photoelasticity measurement); measuring the state of the stress which acts on the measurement target object by measuring light emitted from a substance in response to the stress (mechanoluminescence measurement); and obtaining dynamic information including a stress distribution by arithmetically processing data obtained as a result of the photoelasticity measurement and data obtained as a result of the mechanoluminescence measurement.

Further, the dynamic information may be normal stress component distribution information.

The dynamic information may be shearing stress distribution information.

The dynamic information may be stress direction information.

Further, according to another aspect of the present invention, a stress analysis equipment is provided, including: a photoelasticity measurement means for measuring a state of a stress which acts on a measurement target object by measuring photobirefringence of a substance caused by the stress; a mechanoluminescence measurement means for measuring the state of the stress which acts on the measurement target object by measuring light emitted from a substance in response to the stress; and an arithmetic processing means for obtaining dynamic information including a stress distribution, by arithmetically processing data obtained by the photoelasticity measurement means and data obtained by the mechanoluminescence measurement means.

Further, the dynamic information may be normal stress component distribution information.

The dynamic information may be shearing stress distribution information.

The dynamic information may be stress direction information.

In measuring a stress distribution of an object, it becomes possible to measure a more detailed stress state than can be accomplished using the photoelasticity measurement method alone. For instance, when using the photoelasticity measurement method alone it is impossible to obtain principal stress component values.

BRIEF DESCRIPTION OF THE DRAWINGS

In the accompanying drawings:

FIGS. 1A and 1B are explanatory diagrams according to an exemplary embodiment of the present invention, in which FIG. 1A shows a state where a stress distribution at the time when a load W is applied to a hook as a test piece is measured, and FIG. 1B is a functional block diagram according to an exemplary embodiment of the present invention.

DETAILED DESCRIPTION OF THE EXEMPLARY EMBODIMENTS

The exemplary embodiments of the present invention are realized by performing both photoelasticity stress measurement and mechanoluminescence measurement to measure a stress distribution of an object. By performing arithmetic processing or the like using data obtained as a result of the photoelasticity stress measurement and data obtained as a result of the mechanoluminescence measurement, it becomes possible to obtain stress information that cannot be obtained through only one of the measurements.

Figure 1A:
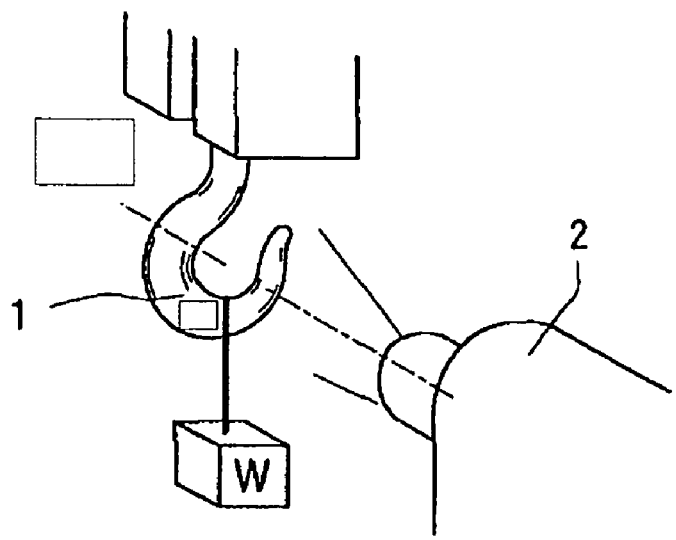

FIG. 1A shows a case where a load W is applied to a hook 1 as a test target piece. That is, in an exemplary embodiment of the present invention, the hook 1 to which the load is applied is photographed with a camera 2, as shown in FIG 1A.

The camera 2 that has conventionally been used in photoelasticity measurement is used to photograph birefringence caused by a stress and a strain that act on the hook 1 (photoelasticity optical system is omitted from the figure). In addition, a substance that emits light in response to a stress is applied to the hook 1 and a state where the substance emits light on receiving the stress is photographed with a camera. Here, the photoelasticity measurement and the mechanoluminescence measurement can be obtained from different cameras or the same camera.

Figure 1B:
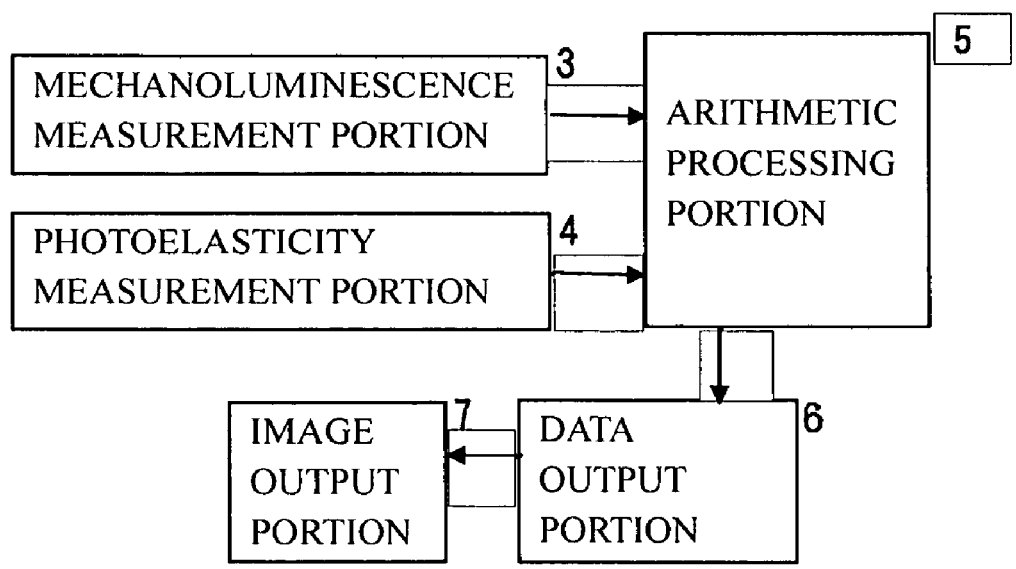

With reference to image data obtained as a result of the photographing as described above, a photoelasticity stress distribution is measured at a photoelasticity stress measurement portion 4 shown in FIG. 1B and a mechanoluminescence distribution is measured at a mechanoluminescence measurement portion 3. Those measurement data items are arithmetically processed at an arithmetic processing portion 5. A result of the arithmetic processing is outputted from a data output portion 6 to an image output portion 7 as, for instance, an image and is displayed on a monitor or the like.

Figure 2:
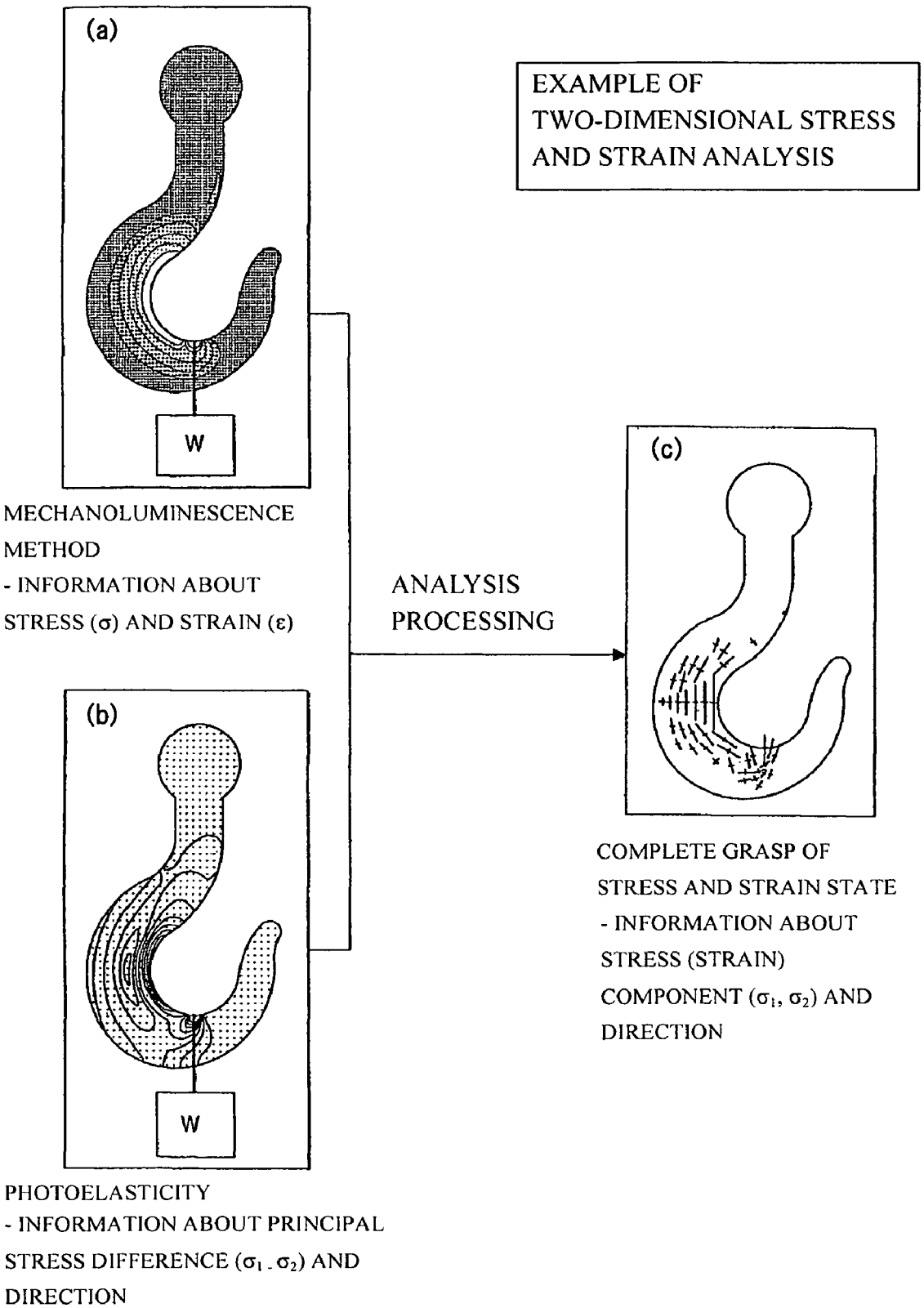
FIG. 2 is an explanatory diagram showing a state where predetermined stress distribution information is obtained by arithmetically processing mechanoluminescence photographed image data and photoelasticity stress photographed image data in an exemplary embodiment of the present invention.

In FIG. 2, an exemplary analysis for the case described above, where the load W is applied to the hook 1, is schematically shown. Mechanoluminescence image data obtained in operation (a) and photoelasticity image data obtained in operation (b) are both arithmetically processed in operation (c), thereby making it possible to obtain stress information, such as individual principal stress component values ($\sigma_1$ and $\sigma_2$), which cannot be obtained with only one of the mechanoluminescence image data and the photoelasticity image data. Hereinafter, an example of basic theory of the exemplary embodiments of the present invention will be described.

It is made possible to acquire physical quantities which cannot be fundamentally measured with only one of the photoelasticity stress measurement method and the mechanoluminescence measurement method, in other words, principal stress component values ($\sigma_1$ and $\sigma_2$) by using the two techniques in combination.

A surface stress of a sample (isotropic elastic body) is examined in a plane stress state. With respect to the principal stresses $\sigma_1$ and $\sigma_2$, it is possible to express strains $\epsilon_1$ and $\epsilon_2$ as follows:

$$\epsilon_1 = (1/E) \times (\sigma_1 - \nu\sigma_2) \tag{5}$$

$$\epsilon_2 = (1/E) \times (\sigma_2 - \nu\sigma_1) \tag{6}$$

where E indicates a modulus of longitudinal elasticity and $\nu$ indicates Poisson's ratio.

Also, elastic energy u is as follows:

$$u = (1/2) \times (\sigma_1 \epsilon_1 + \sigma_2 \epsilon_2) \tag{7}$$

Therefore, when Equations (5) and (6) are substituted into Equation (7), the following equations are obtained:

$$u = (1/2E) \times (\sigma_1^2 + \sigma_2^2) - \nu/E \times \sigma_1 \sigma_2 \tag{8}$$

$$= (1/2E) \times (\sigma_1^2 + \sigma_2^2 - 2\nu\sigma_1\sigma_2) \tag{9}$$

$$= (1/2E) \times ((\sigma_1 + \sigma_2)^2 - 2\sigma_1\sigma_2 - 2\nu\sigma_1\sigma_2) \tag{10}$$

Also, it is possible to measure a principal stress difference with the photoelasticity measurement method, so when a value that can be obtained is referred to as "A" and the following Equations (11) and (12) are substituted into Equation (6):

$$\sigma_1 - \sigma_2 = A \quad (11)$$

$$\sigma_2 = -A + \sigma_1 \quad (12)$$

Equation (13) given below is obtained:

$$u = [((1-v)/E) \times \sigma_1^2] - [(A(1-v)/E) \times \sigma_1] + (A^2/2E) \quad (13)$$

When this equation is modified, a quadratic equation concerning $\sigma_1$ is obtained as follows:

$$[((1+v)/E) \times \sigma_1^2] - [(A(1+v)/E) \times \sigma_1] + ((A^2/2E) - u) = 0 \quad (14)$$

The elastic energy u is information that can be obtained with the mechanoluminescence method, so all of the following three coefficients of this equation become known values:

$$(1-v)/E = B \quad (15)$$

$$-A(1-v)/E = C \quad (16)$$

$$(A^2/2E) - u = D \quad (17)$$

Accordingly, when Equation (10) that is a quadratic equation concerning $\sigma_1$ is solved, it is possible to obtain the following solutions:

$$\sigma_1 = (-C \pm (C^2 - 4BD)^{1/2})/(2B) \quad (18)$$

$$\sigma_2 = A - \sigma_1 \quad (19)$$

It is possible to uniquely determine plus/minus signs in Equation (14) from absolute values or calibration. Note that this result can also be expressed as follows:

$$(\sigma 1, \sigma_2) = (-C \pm (C^2 - 4BD)^{1/2})/(2B) \quad (20)$$

It is possible to carry out the process described above based on a two-dimensional image obtained with the photoelasticity measurement method and the mechanoluminescence method, and to present a result of the process in the form of an image. Also, when a principal stress direction that can be found with the photoelasticity measurement method and the result of the process are combined with each other, complete stress information, which includes individual principal stress components and the principal stress direction, becomes clear.

The exemplary embodiments of the present invention are usable in various fields in which it is preferable to measure a stress distribution. For instance, when a mechanoluminescent substance is applied to a product or a model created with three-dimensional modeling equipment or the like through mixing, application, or the like and the photoelasticity measurement and the mechanoluminescence measurement are performed, it becomes possible to perform a detailed surface stress analysis, confirmation of a stress concentrated area, or the like for the sake of, for instance, prevention of breakage or a fatigue failure.

Also, for instance, when a mechanoluminescent substance is applied to a component, a model, or the like created by performing cutting machining or the like through application or the like and the photoelasticity measurement and the mechanoluminescence measurement are performed, a detailed surface stress analysis becomes possible. Consequently, it becomes possible to perform confirmation of a stress concentrated area for the sake of, for instance, prevention of breakage or a fatigue failure.

Further, accuracy of a simulation based on a finite element method or the like depends on a degree of similarity between boundary conditions set for the simulation and those of an actual object. It is possible to improve the accuracy of the simulation by confirming stress components of the actual object and a model through the photoelasticity measurement and mechanoluminescent measurement and optimizing the boundary conditions or the like of the simulation.

Still further, for instance, when the measurement is performed for a simulation bone fitted with an orthopedic or dental implant, it becomes possible to obtain a detailed surface stress distribution of the implant, which enables a more detailed dynamic compatibility evaluation of the implant.

Also, for instance, when the photoelasticity measurement and the mechanoluminescence measurement are performed using a magnifying optical system such as a microscope, a high-precision stress analysis of a minute area (such as micromachine) which cannot be measured with a conventional technique becomes possible.

Also, when an optically transparent material is used in both of the techniques, it becomes possible to measure not only a surface stress but also an internal stress.

Needless to say, it is possible to supplement the method of the exemplary embodiments with a stress measurement method, such as a strain gage method, for the sake of calibration or the like.

The exemplary embodiments of present invention enable detailed stress distribution measurement that cannot be provided by the photoelasticity method alone and, therefore, are usable in various industrial fields in which stress measurement is required.

What is claimed is:

1. A stress analysis method, comprising:
   measuring a state of a stress which acts on a measurement target object by measuring photobirefringence of a first substance caused by the stress;
   measuring the state of the stress which acts on the measurement target object by measuring light emitted from a second substance in response to the stress; and
   obtaining dynamic information including a stress distribution by arithmetically processing data obtained as a result of the photoelasticity measurement and data obtained as a result of the mechanoluminescence measurement.

2. A stress analysis method according to claim 1, wherein the dynamic information comprises normal stress component distribution information.

3. A stress analysis method according to claim 1, wherein the dynamic information comprises shearing stress distribution information.

4. A stress analysis method according to claim 1, wherein the dynamic information comprises stress direction information.

5. A stress analysis equipment, comprising:
   a photoelasticity measurement means for measuring a state of a stress which acts on a measurement target object by measuring photobirefringence of a first substance caused by the stress;
   a mechanoluminescence measurement means for measuring the state of the stress which acts on the measurement target object by measuring light emitted from a second substance in response to the stress; and an arithmetic processing means for obtaining dynamic information including a stress distribution by arithmetically processing data obtained by the photoelasticity measurement means and data obtained by the mechanoluminescence measurement means.

6. A stress analysis equipment according to claim 5, wherein the dynamic information comprises normal stress component distribution information.

7. A stress analysis equipment according to claim 5, wherein the dynamic information comprises shearing stress distribution information.

8. A stress analysis equipment according to claim 5, wherein the dynamic information comprises stress direction information.

* * * * *